United States Patent

Parker et al.

[11] Patent Number: 5,843,866
[45] Date of Patent: Dec. 1, 1998

[54] PESTICIDAL COMPOSITIONS COMPRISING SOLUTIONS OF POLYUREA AND/OR POLYURETHANE

[75] Inventors: Brian A. Parker, Wexford, Ireland; Longin V. Holejko, Arlington, Mass.; Barry A. Cullen, Lyndeborough, N.H.; Jonathan D. Davis, Malden, Mass.

[73] Assignee: Hampshire Chemical Corp., Lexington, Mass.

[21] Appl. No.: 693,375

[22] Filed: Aug. 5, 1996

Related U.S. Application Data

[63] Continuation-in-part of Ser. No. 368,204, Dec. 30, 1994, Pat. No. 5,543,383.

[51] Int. Cl.[6] .................................................. A01N 25/24
[52] U.S. Cl. .................... 504/116; 71/DIG. 1; 424/407; 514/788.1; 514/975
[58] Field of Search .................... 504/116; 71/DIG. 1; 424/407; 514/975, 788.1

[56] References Cited

U.S. PATENT DOCUMENTS

| | | | |
|---|---|---|---|
| 4,129,435 | 12/1978 | Takematsu et al. | 71/65 |
| 4,155,892 | 5/1979 | Emmons et al. | 71/69 |
| 4,405,360 | 9/1983 | Cardarelli | 71/117 |
| 4,405,531 | 9/1983 | Franz | 260/501.12 |
| 4,761,176 | 8/1988 | Alt | 71/118 |
| 4,886,866 | 12/1989 | Braatz et al. | 528/59 |
| 4,936,901 | 6/1990 | Surgant, Sr. et al. | 71/92 |
| 5,059,704 | 10/1991 | Petroff et al. | 556/437 |
| 5,091,176 | 2/1992 | Braatz et al. | 424/78.17 |
| 5,118,338 | 6/1992 | Moller | 71/86 |
| 5,180,414 | 1/1993 | Darchy et al. | 504/206 |
| 5,196,044 | 3/1993 | Caulder et al. | 504/127 |
| 5,258,359 | 11/1993 | Kassebaum et al. | 504/206 |
| 5,362,705 | 11/1994 | Moucharafieh et al. | 504/206 |

*Primary Examiner*—S. Mark Clardy
*Attorney, Agent, or Firm*—Nields, Lemack & Dingman

[57] ABSTRACT

A pesticidal composition including isocyanate capped high molecular weight diols, triols and polyols. A pesticide and water are combined with hydrophilic isocyanate end-capped prepolymers in order to significantly improve the efficacy of the pesticide. The liquid pesticidal compositions of the present invention can be prepared by simply mixing the various constituents. The order of addition can be used effectively to cap free isocyanate groups in the hydrophilic prepolymer.

17 Claims, 3 Drawing Sheets

PESTICIDAL COMPOSITIONS COMPRISING SOLUTIONS OF POLYUREA AND/OR POLYURETHANE

This application is a continuation-in-part of U.S. Ser. No. 08/368,204 filed on Dec. 30, 1994 now U.S. Pat. No. 5,543,383.

BACKGROUND OF THE INVENTION

Glyphosate, or N-phosphonomethylglycine ($HOOCCH_2NHCH_2PO(OH)_2$), is a well-known translocated, postemergence, broadspectrum herbicide. The typical commercial formulation contains about 41% of the isopropylamine salt of glyphosate and is believed to contain about 12% by weight of a tallow amine ethoxylate surfactant. Glyphosate is a relatively insoluble acid, and thus is typically formulated and applied as a salt, such as the isopropylamine, sodium or ammonium salt.

Surfactants are typically incorporated into the formulation to improve the activity of the glyphosate. However, the term "surfactant" is ambiguous, as the form supplied by manufacturers is not necessarily a single compound, but can be a mixture. For example, with ethoxylated surfactants, the degree of ethoxylation can be and typically is a statistical mixture. The literature describes use of surfactants in glyphosate compositions and in particular, *Weed Science*, Vol. 25, pp 275–287 (1977) demonstrates the necessity of including a surfactant in glyphosate formulations. Conventional glyphosate formulations include the use of surfactants such as siloxanes to enhance the rainfast properties of glyphosate formulations. However, commercialization of such formulations has been hindered by the cost of incorporation of such surfactants into the formulations, and by the hydrolytic instability of such adjuvants. Other formulations including surfactants are disclosed in U.S. Pat. Nos. 5,362,705, 5,180,414 and 5,118,338.

In addition, in view of the recent environmental concerns surrounding the use of chemical pesticides and the possibility that residuals thereof might contaminate food, ground water, etc., a substantial reduction in the amount of pesticide necessary to be effective would be highly desirable.

It is therefore an object of the present invention to improve the rainfast properties of pesticide formulations without the use of siloxane surfactants.

It is a further object of the present invention to enhance the efficacy of these formulations in an environmentally friendly manner.

SUMMARY OF THE INVENTION

The problems of the prior art have been solved by the present invention, which relates to a pesticidal composition including isocyanate capped high molecular weight diols, triols and polyols. More specifically, the present invention relates to a pesticidal composition in which a pesticide is combined with hydrophilic isocyanate end-capped prepolymers in order to significantly improve the efficacy of the pesticide. A combination of surfactant, pesticide, and a hydrated polymer or hydrophilic prepolymer consisting of isocyanate capped prepolymers which are substantially comprised of ethylene oxide, propylene oxide or butylene oxide units or a combination thereof demonstrates increased efficacy over conventional pesticide formulations. The pesticidal compositions of the present invention also exhibit controlled release, thereby enhancing its efficacy. The liquid compositions of the present invention can be prepared by simply mixing the various constituents. The order of addition can be used effectively, if desired, to cap free isocyanate groups in the hydrophilic prepolymer. Hydrophilic prepolymers consisting of isocyanate capped prepolymers which are substantially comprised of ethylene oxide, propylene oxide or butylene oxide units or a combination thereof are described in the art as hydratable or water soluble. See Braatz et al., U.S. Pat. Nos. 4,886,866 and 5,091,176, the disclosure of which are hereby incorporated by reference. In one embodiment, the water soluble prepolymer can be covalently bonded to an amine group if present in the pesticide (such as glyphosate), or to the alcohol group in the pesticide (such as dicofol (sold commercially as "Kelthane")). In another embodiment, the prepolymer can be reacted with water to form polyurethane and polyurea-urethane polymer gels prior to the incorporation of the pesticide. In a still further embodiment, the prepolymer can form a reaction product with a surfactant via a covalent linkage between the isocyanate groups of the prepolymer and a reactive group on the surfactant.

DETAILED DESCRIPTION OF THE INVENTION

The term "pesticide" or "economic poison" as used herein means any substance or mixture of substances intended for preventing, destroying, repelling or mitigating any insects, rodents, nematodes, fungi, or weeds, or, any other forms of life declared to be pests; and any substance or mixture of substances intended for use as a plant regulator, defoliant, or desiccant.

Suitable herbicides that can be used in the present invention, either alone or in combination, include phenoxy acids (acids, esters, salts), benzoic acid, aryloxy phenoxypropionate (acids, ester, salts), sulfonyl ureas (acids, esters), imidazilinones, bipyridillium, diphenyl ether (acids, salts), 2,4-D salts and esters, cyclohexanedione, methane arsonate, triazines, aliphatic carboxylic acids, lactofen, linuron, glyphosate, paraquat, bifenox, benzonitrile, carbamate, thiocarbamate, PYRAZONE, GLUFOSINATE, DESMEDIPHAM, TRICLOPYR, CLOPYRALID, QUINCLORAC, ETHIOZIN, PICHLORAM, BENTAZON, AMITROLE, ATRIZINE, METRIBUZIN, PHENMEDIPHAM, CHLORMETQUAT, UNICONAZOLE, PRIMISULFURON, BROMOXYNIL and the like.

Suitable insecticides and nematocides include alpha-cypermethrin, azadiractin, butocarboxim, diazinon, demeton-s-methyl, phorate, cycloprate, propargite and the like.

Suitable fungicides include thiabendazole, captan, chlorothalonil, copper salts, mancozeb, procymidone, triforine, tebuconazole and the like.

Suitable acaricides include tetradifon, pyridiben, methamidophos, flucycloxuron and the like.

Suitable plant growth regulators include maleic hydrazide, gibberellic acid, uniconizole, chlormequat chloride, naphthaleneacetamide, ancymidol, ethychlozate and the like.

Those skilled in the art will recognize that various pesticides may be used in combination, depending upon the effect desired.

Suitable surfactants or wetting agents are those conventional in the art, as described in U.S. Pat. No. 3,853,530, the disclosure of which is hereby incorporated by reference. Such surfactants include alkyl benzene and alkyl naphthalene sulfonates, alkyl phenol polyoxyethylene, sulfated fatty alcohols, amines or acid amides, long chain acid esters of sodium isethionate, esters of sodium sulfosuccinate, sulfated or sulfonated fatty acid esters petroleum sulfonates, N-acyl amino acids such as sarcosinates, alkyl polyglycosides, alkyl ethoxylated amines such as tallow amine ethoxylate, and the like. The surfactants may also include additives such as glycols including polyethylene glycol, diethylene glycol, ethylene glycol, alcohols such as methanol, ethanol, 2-propanol, n-propanol, butanol, hexanol, heptanol and siloxanes, etc. and mixtures of the aforementioned additives.

The prepolymers used as a starting material in the instant invention provide hydrated polyurethane, polyurea-urethane and polyurea polymer gels. Numerous polyurethane polymers have been previously identified. Many hydrogel polymers, prepared from various prepolymers, have been prepared and used for a wide variety of applications. Typically, hydrogels are formed by polymerizing a hydrophilic monomer in an aqueous solution under conditions such that the prepolymer becomes crosslinked, forming a three-dimensional polymeric network which gels the solution in concentrated form. Polyurethane hydrogels are formed by polymerization of isocyanate-end capped prepolymers to create urea and urethane linkages. More specifically, the prepolymers are prepared from solutions of high molecular weight isocyanate end-capped prepolymers substantially or exclusively comprised of ethylene oxide, propylene oxide or butylene oxide units, or mixtures thereof. Preferably the prepolymers are derived from polymeric monomer units (the prepolymer units) at least 75% of which are oxyethylene-based diols or polyols having molecular weights of about 100 to about 30,000, preferably 7000 to 30,000, with essentially all of the hydroxyl groups of these diols or polyols capped with polyisocyanate. Suitable polyols include triols such as glycerol, trimethylol-propane, trimethylolethane and triethanolamine. The prepolymers useful in the invention are prepared by reacting the selected diols, triols or polyols with polyisocyanate at an isocyanate-to-hydroxyl ratio of about 1.8 to about 2.2 so that essentially all of the hydroxyl groups are capped with polyisocyanate. Aromatic, aliphatic or cycloaliphatic polyisocyanates may be used. The use of aliphatic polyisocyanates permits a greater degree of handling and/or shaping since aliphatic isocyanate-capped prepolymers typically require about 20 to 90 minutes to gel to a hydrated polymer state. Prepolymers capped with aromatic polyisocyanates gel more rapidly, in about 30 to 60 seconds. Aliphatic polyisocyanates are also preferred in view of decreased toxicological considerations. Examples of suitable di- and polyfunctional isocyanates are as follows: toluene-2,4-diisocyanate, toluene-2,6-diisocyanate, commercial mixtures of toluene-2,4 and 2,6-diisocyanate, isophorone diisocyanate, ethylene diisocyanate, ethylidene diisocyanate, propylene-1,2-diisocyanate, cyclohexylene-1,2-diisocyanate, cyclohexylene-1,4-diisocyanate, m-phenylene diisocyanate, 3,3"-diphenyl-4,4"-biphenylene diisocyanate, 1,6-hexamethylene diisocyanate, 1,4-tetramethylene diisocyanate, 1,10-decamethylene diisocyanate, cumene-2,4-diisocyanate, 1,5-naphthalene diisocyanate, methylene dicyclohexyl diisocyanate, 1,4-cyclohexylene diisocyanate, p-tetramethyl xylylene diisocyanate, p-phenylene diisocyanate, 4-methoxy-1,3-phenylene diisocyanate, 4-chloro-1,3-phenylene diisocyanate, 4-bromo-1,3-phenylene diisocyanate, 4-ethoxy-1,3-phenylene di-isocyanate, 2,4-dimethyl-1,3-phenylene diisocyanate, 2,4-dimethyl-1,3-phenylene diisocyanate, 5,6-dimethyl-1,3-phenylene di-isocyanate, 2,4-diisocyanatodiphenylether, 4,4'-diisocyanatodi-phenylether, benzidine diisocyanate, 4,6-dimethyl-1,3-phenylene diisocyanate, 9,10-anthracene diisocyanate, 4,4'-diisocyanatodi-benzyl, 3,3'-dimethyl-4,4'-diisocyanatodiphenylmethane, 2,6-dimethyl-4,4'-diisocyanatodiphenyl, 2,4-diisocyanatostilbene, 3,3'-dimethoxy-4,4'-diisocyanatodiphenyl, 1,4-antracenediisocyanate, 2,5-fluorenediisocyanate, 1,8-naphthalene diisocyanate, 2,6-diisocyanatobenzfuran, 2,4,6-toluene triisocyanate, p,p',p"-triphenylmethane triisocyanate, trifunctional trimer (isocyanurate) of isophorone diisocyanate, trifunctional biuret of hexamethylene diisocyanate, trifunctional trimer (isocyanurate) of hexamethylene diisocyanate, polymeric 4,4'-diphenylmethane diisocyanate, xylylene diisocyanate and m-tetramethyl xylylene diisocyanate.

Capping of the selected diols or polyols with polyisocyanates to form prepolymers for use in the present invention is effected using stoichiometric amounts of reactants. The isocyanate-to-hydroxyl group ratio should be between about 0.01 and about 10, preferably 0.1 to 3, most preferably 0.2 to 2.2. Higher ratios may be used but are not preferred since they may lead to problems associated with excessive monomer present in the final products. The capping reaction may be by any convenient method or procedure, such as at about 20° to about 150° C., under dry nitrogen, for about 2 hours to about 14 days, preferably in the absence of a catalyst. The preferred temperature is about 60° to 100° C. The reaction is terminated when the isocyanate concentration approximates theoretical values.

Preferred prepolymers include toluene diisocyanate-polyethylene glycol-timethylolpropane, methylene diisocyanate-methylene diisocyanate homopolymer-polymeric methylene diisocyanate -polyethylene glycol, toluene diisocyanate and polymer of ethylene oxide and propylene oxide with trimethylolpropane, isophorone diisocyanate and polymer of ethylene oxide-propylene oxide-trimethylolpropane, toluene diisocyanate polyethylene glycol trilactate, and polyethylene glycol end capped with toluene diisocyanate. Such prepolymers are available under the tradename HYPOL® from Hampshire Chemical Corp., and include HYPOL® PreMA®, HYPOL® 2000, HYPOL® 3000, HYPOL® 4000, HYPOL® 5000, and biodegradable HYPOL®.

Typically the ratio of pesticide to prepolymer is from about 0.001 to about 10.

In the case of glyphosate, for example, neutralization of the glyphosate acid to form a herbicidally active glyphosate derivative can be effectuated with any suitable base, including alkali metal, alkali earth metal and ammonium hydroxides and alkyl amines. Preferred glyphosate salts upon neutralization include the mono(trimethylamine) salt of N-phosphonomethylglycine, the mono(diethylenetriamine) salt of N-phosphonomethylglycine, the monoisopropylamine salt of N-phosphonomethylglycine, the mono-n-propylamine salt of N-phosphonomethylglycine, the mono (tallowamine) salt of N-phosphonomethylglycine, the monosodium salt of N-phosphonomethylglycine and the monopotassium salt of N-phosphonomethylglycine. Those skilled in the art will readily appreciate that the corresponding di- and tri-salts of N-phosphonomethylglycine also can be prepared by increasing the amount of base added accordingly.

In the first embodiment of the present invention, the prepolymer can be incorporated into solution as a reaction product with water. The amount of prepolymer used should be low enough so as to avoid immediate gel formation. Generally less than about 20% by weight is suitable, more preferably about 2 to 10% by weight, most preferably about 3 to 7% by weight. If higher amounts of prepolymer are desired, primary or secondary alkyl amine can be added to help prevent gel formation. Preferably the reaction is carried out from just above the freezing point of water to about room temperature. Higher temperature may be used, although they enhance the rate of gel formation. The pesticide is added after the prepolymer/water reaction is complete. The amount of pesticide used will depend upon the amount desired in the final formulation, and can generally vary from about 0.1% to above 80% by weight. A clear, stable solution or suspension is obtained. In the case of glyphosate, the current commercial formulation employs about 36% glyphosate acid (41% as the isopropylamine salt). The addition of glyphosate acid results in the formation of a white slurry. The slurry is neutralized with any suitable base, preferably a hydroxide such as sodium, potassium or ammonium hydroxide, most preferably isopropylamine. Preferably sufficient base is added to form the monosalt, although the di and tri-salts can also be formed upon addition of additional base.

Surfactant can be added at any point after the reaction of the prepolymer with water, i.e., immediately prior to pesticide addition, immediately prior to neutralization, or after neutralization. Preferably the amount of surfactant added is from about 0.1 to about 20% (wt/wt) of pesticide, with the actual amounts depending upon the identify of the surfactant used. Upon evaporation of water, strong elastic films are obtained. These films are hydratable water-insoluble films which form after spray application of the formulation to the substrate. Such hydratable films are desirous since they minimize or prevent the pesticide from washing off the surface of the substrate being sprayed (such as a plant leaf). These hydratable films also greatly enhance the rainfastness of the formulation.

In the second embodiment of the present invention, applicable to pesticides having a reactive group capable of forming a covalent bond with the prepolymer, the prepolymer is incorporated into the formulation as a reaction product covalently bonded with the pesticide. Specifically, in the case of glyphosate, glyphosate acid is added directly to the prepolymer, and reacts with the free isocyanate groups present in the prepolymer to cap the same. Either partial or complete capping of the isocyanate groups can be obtained, depending upon the relative amount of glyphosate used. The resulting reaction product is neutralized with a suitable base as in the first embodiment. Surfactant can be added prior to or after neutralization. Amounts of constituents used are similar to those disclosed above with respect to the first embodiment.

In the third embodiment of the present invention, the hydrophilic isocyanate end-capped prepolymers are incorporated as a reaction product with a surfactant via a covalent linkage between the isocyanate (—NCO) groups of the polymer and reactive groups typically available on surfactants, such as reactive primary or secondary amine (—NH, —NH$_2$) groups, sulfhydryl (—SH) groups, hydroxyl (—OH) groups and carboxylate (—COOH) groups. As in the second embodiment, the capping of the free isocyanate groups in the prepolymer can be partial or complete, depending upon the relative amounts of reactants used. Preferably the surfactant is an alkyl ethoxylated amine that may include alkyl or alkylarylethoxylates, including a mixture of polyethylene glycol, diethylene glycol and ethylene glycol. The pesticide is then added. In some cases suitable cationic or anionic surfactants may be used. Amounts of constituents used are similar to those disclosed above with respect to the first embodiment.

The formulations of the present invention are preferably spray-applied to above-ground portions of the plants. The concentration of active ingredient should be present in a pesticidally effective amounts, which depends on the particular pesticide and pest and the desired response.

EXAMPLE 1

At room temperature, 28 grams of HYPOL® PreMA® G-50 hydrophilic prepolymer were added to 972 grams of water. The solution was stirred for two hours to ensure complete reaction of the prepolymer with the water. 100 grams of glyphosate acid was added, and the pH was adjusted to 4.8 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 2

At room temperature, 30 grams of HYPOL® PreMA® G-50 hydrophilic prepolymer were added to a mixture of alkylamineethoxylate (62.5 g) and water (907.5 g). The solution was stirred for two hours. 150 grams of glyphosate acid was added and the solution was neutralized with isopropylamine to a pH of 4.8. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 3

At room temperature, 42 grams of a surfactant comprising about 50% tallow amine ethoxylate (15 moles ethoxylate), 20% polyethylene glycol (molecular weight 600) and 30% ethylene and diethylene glycol were added to 928 grams of water. 30 grams of HYPOL® PreMA® G-50 hydrophilic prepolymer were added and allowed to mix for two hours. 150 grams of glyphosate acid were added and the pH was adjusted with isopropylamine to 4.8. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 4

At room temperature, 62.5 grams of a surfactant comprising about 50% tallow amine ethoxylate (15 moles ethoxylate), 20% polyethylene glycol (molecular weight 600) and 30% ethylene and diethylene glycol were mixed with 877.5 grams of water. 60 grams of HYPOL® PreMA® G-50 were added to the mixture and allowed to stir for three hours. 150 grams of glyphosate acid were mixed for 30 minutes into the resulting solution. The slurry was neutralized with isopropylamine to a pH of 4.8. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 5

At room temperature, 42 grams of a surfactant comprising about 50% tallow amine ethoxylate (15 moles ethoxylate), 20% polyethylene glycol (molecular weight 600) and 30% ethylene and diethylene glycol were mixed with 897.5 grams of water. 60 grams of HYPOL® PreMA® G-50 were added to this mixture and the solution was stirred for two hours. 150 grams of glyphosate acid were then added and the slurry neutralized to a pH of 4.8 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 6

At room temperature, 28 grams of HYPOL® PreMA® G-50 hydrophilic prepolymer were added to 972 grams of water. The mixture was allowed to stir for 3 hours. 100 grams of glyphosate acid were added to this solution and the pH was adjusted to 4.8 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 7

At room temperature, 30 grams of HYPOL® PreMA® G-50 hydrophilic prepolymer were added to 907.5 grams of water. The solution was allowed to stir for 60 minutes. 150 grams of glyphosate acid were added, followed by 62.5 grams of Toximal TA-15 surfactant. The pH was adjusted from 2.85 to 4.1 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 8

At room temperature, 60 grams of HYPOL® PreMA® G-50 hydrophilic prepolymer were added to 870 grams of water. The solution was allowed to stir for 60 minutes. 150 grams of glyphosate acid were added, followed by 62.5 grams of Toximal TA-15 surfactant. The pH was adjusted to 3.85 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 9

At room temperature, 15 grams of glyphosate acid were slurried in 90 grams of water. 3 grams of HYPOL® PreMA® G-50 were added to this slurry and allowed to mix for one hour. 6 grams of Toximal TA-15 surfactant were then added and the contents neutralized to a pH of 4.0 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 10

At room temperature, 20 grams of glyphosate acid were slurried in 85 grams of water. 3 grams of HYPOL® PreMA® G-50 hydrophilic prepolymer were added to this slurry and allowed to mix for 61 minutes. 6 grams of Toximal TA-15 surfactant were then added and the contents neutralized to a pH of 4.7 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 11

At room temperature, 36 grams of glyphosate acid were slurried in 69 grams of water. 3.3 grams of HYPOL® PreMA® G-50 hydrophilic prepolymer were added to this slurry and allowed to stir for 65 minutes. 6 grams of Toximal TA-15 surfactant were then added and the contents neutralized to a pH of 5.0 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 12

At room temperature, 62.5 grams of a surfactant comprising about 50% tallow amine ethoxylate (15 moles ethoxylate), 20% polyethylene glycol (molecular weight 600) and 30% ethylene and diethylene glycol were stirred into 907.0 grams of water. 60 grams of HYPOL® PreMA® G-50 hydrophilic prepolymer were added to this mixture and the contents were allowed to mix for 47 minutes. 109.6 grams of glyphosate acid were then added and the contents were neutralized to a pH of 4.75 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 13

At room temperature, 30 grams of HYPOL® PreMA® G-50 hydrophilic prepolymer were mixed for 45 minutes with 907.5 grams of water. 42 grams of a surfactant comprising about 50% tallow amine ethoxylate (15 moles ethoxylate), 20% polyethylene glycol (molecular weight 600) and 30% ethylene and diethylene glycol were then added and the solution was mixed for another 45 minutes. 109.6 grams of glyphosate acid were added, and the contents neutralized to a pH of 4.64 with isopropylamine. A stable, clear solution was obtained.

Approximately 25% of the solution was allowed to dry in a fume hood overnight. A strong elastic film was obtained.

A portion of the solution was diluted to approximately 1% glyphosate acid equivalent with 50 mls. of water and also allowed to dry in a fume hood overnight. A strong elastic film was obtained.

EXAMPLE 14

Figure 1:
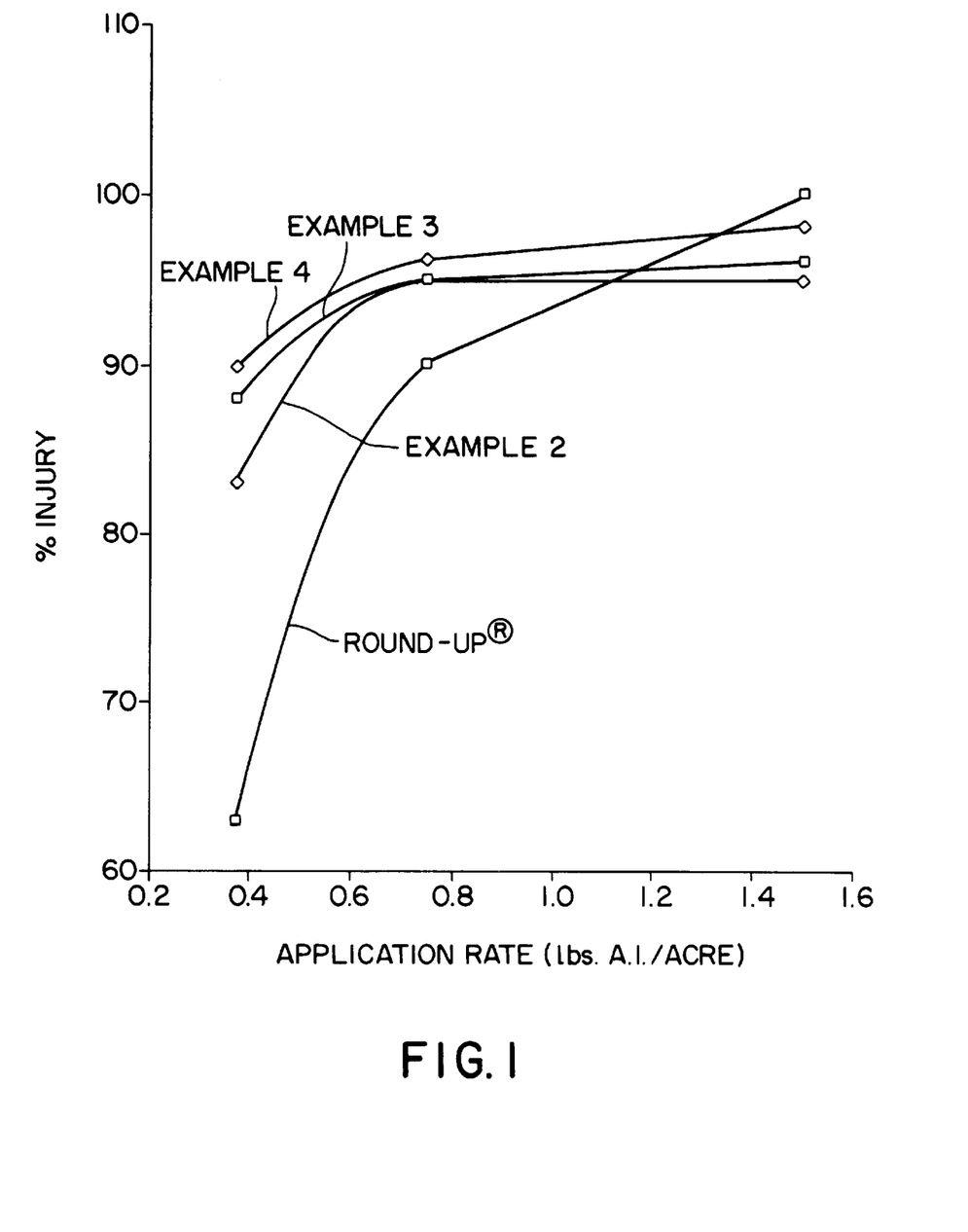
FIG. 1 is a graph comparing dose response of formulations of the present invention to commercial grade Round-up® herbicide after 28 days.
Figure 2:
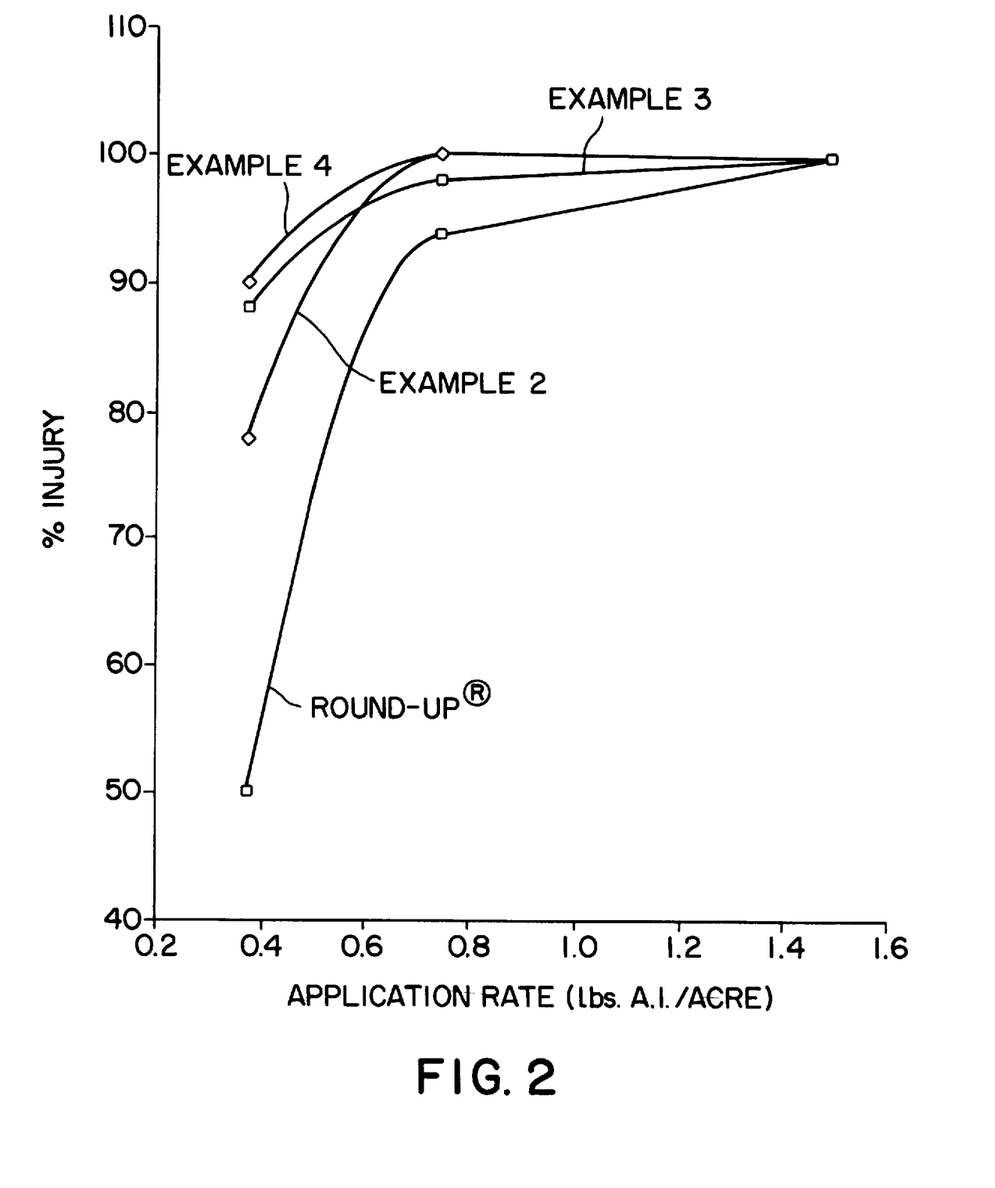
FIG. 2 is a graph comparing dose response of formulations of the present invention to commercial grade Round-up® herbicide after 42 days.

A dose response study was conducted during the summer/fall months to evaluate the efficacy of the present invention, and the results are shown in FIGS. 1 and 2. The experimental design was a randomized complete block with four replications. Plant injury was evaluated visually every week during the study.

Bermudagrass was sprayed with the formulations of Examples 2, 3 and 4, as well as the commercial grade Round-up®, at 0.375, 0.75 and 1.5 lb of active ingredient per acre. Commercial Round-up® effectively controlled Bermudagrass at the two higher rate applications (0.75 and 1.5 lb/acre). At these higher concentrations, all the formulations shown in FIGS. 1 and 2 demonstrated a high degree of injury to Bermudagrass. Shoot fresh weight data confirmed the injury ratings. The formulations of the present invention were more effective in reducing Bermudagrass shoot weight than commercial Round-up® when applied at 0.375 lb/acre, and were virtually equivalent to Round-up® herbicide at the two higher concentrations.

EXAMPLE 15

Figure 3:
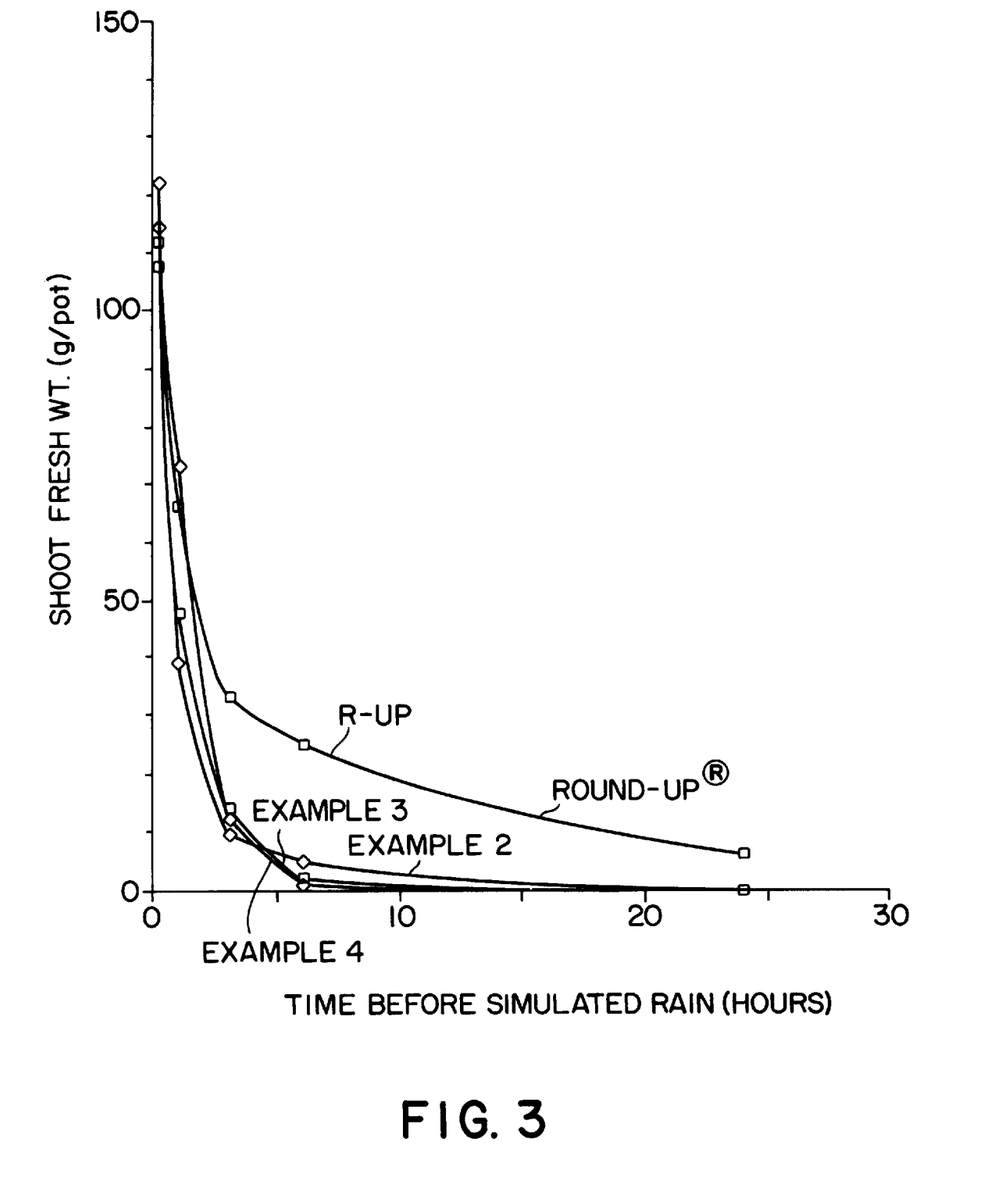
FIG. 3 is a graph comparing shoot fresh weight of Bermudagrass after application of formulations of the present invention and of commercial grade Round-up® herbicide after 70 days.

A simulated rainfall was applied at 15 minutes, 1 hour, 3 hours, 6 hours and 24 hours after formulation application, and the results are shown in FIG. 3. The formulations of Examples 2, 3 and 4 of the present invention significantly outperformed commercial Round-up® herbicide.

EXAMPLE 16

Samples from Examples 2, 3 and 4 above were sprayed in a tropical environment to test the efficacy in hot humid conditions. The samples were sprayed in 2 meter×20 meter plots, with a 1 meter plot buffer zone maintained between plots. Plots were marked with string and stakes.

The weed variety in the plots was noted prior to application and was defined as follows:

30–40% broadleaf
58–68% grasses
2% elusive indica

Climatic conditions during spray application were noted as follows:
Temperature: 30° C.
Humidity: 75%
Full sun on numbered plots
Light to zero wind
Little weather change over two hour spray time A Solo motorized pump spray (air pressured) was employed to spray the plots. A fan jet 564 nozzle and a walking speed of 40 meters/minute was noted. 2 kg pressure was measured in the tank.

Duplicate samples were tested for both dosage response and rainfast properties. The plots were observed after 3 weeks, and all weeks were completely dead. The dosage response and rainfast results are as follows at a 3-month interval:

TABLE 1

TABLE 1

| SAMPLE | RATE (l/hectare) | VISUALS/WEEDS REMAINING |
|---|---|---|
| Example 2 | 4.5 | Some broadleaf 60–70% kill No grass regrowth, 85–98% kill |
| Example 3 | 4.5 | About 50–60% broadleaf kill No grass regrowth, 95–98% kill |
| Example 4 | 4.5 | Very few broadleaves remain, 94–95% kill, 5–6% regrowth. No grass regrowth, 100% kill |
| SPARK® | 6 | 70% regrowth of broadleaf, 30% kill 25–35% grasses regrow |
| ROUND-UP® | 4.5 | Almost total regrowth of all weeds |

TABLE 2

TABLE 2

| | RAINFASTNESS | | |
|---|---|---|---|
| SAMPLE | RATE (l/hectare) | WATER TIME AFTER SPRAYING | VISUALS |
| Example 2 | 4.5 | 1.5 hours | Some regrowth |
| Example 3 | 4.5 | 1.5 hours | No grass regrowth; some broadleaf regrowth |
| Example 4 | 4.5 | 1.5 hours | Only two broadleaf plants found in plot. No grasses found. Essentially complete kill. |

The watered plots were also observed after 3 weeks of spraying. The grasses in the plots were only yellow and were not yet brown or dead.

At the end of 6 weeks, all weeds in all plots were dead. At 6–7 months, preliminary data indicated that plots sprayed with samples from Examples 2, 3 and 4 were still exhibiting herbicidal activity and little regrowth was observed.

EXAMPLE 17

In another plot, the sample from Example 4 was sprayed. The plot was split in half, with the second half only being watered at 1.5 hours after spraying at an approximate rate of 10 liters/plot of water to simulate rainfall. After 6 weeks, all weeds in both plots were dead. At 3 months, both sides of the plot were equally dead. No difference between the watered and unwatered side was observed.

EXAMPLE 18

Two grams of HYPOL® 2000 prepolymer were added to 95 g of water. The solution was stirred for 50 minutes. Two grams of lauroyl sodium sarcosinate were then added to the solution. Twelve grams of glyphosate acid were added and the solution was neutralized with isopropylamine to a pH of approximately 4.8. A clear colorless solution exhibiting some viscosity was obtained.

EXAMPLE 19

Into 98 grams of water, 5 grams of glyphosate acid were added. After 30 minutes of stirring, 2 grams of HYPOL® 2000 prepolymer were added. The solution was then neutralized with 10% wt/wt sodium hydroxide to a pH of 4.3. A clear, stable solution was formed that was very liquid, indicating the compatibility of the components.

EXAMPLE 20

Three grams of HYPOL® PreMA® G-50 hydrophilic prepolymer were added to 97 grams of water and the solution was heated uniformly from 27° C. to 46° C. over 30 minutes. The solution thickened but did not gel. The contents were stirred on a cold magnetic stir plate for another 34 minutes. At 36° C., 5 grams of glyphosate acid were added and the contents neutralized with isopropylamine to a pH of 4.6.

The contents were split in half, with one half stored as a retainer and the other dried in a fume hood over 5 hours. A thin tough film formed which rehydrated, upon the addition of water, to a thick undissolvable skin. The content s were covered and allowed to stand overnight at room temperature. The skin did not redissolve.

EXAMPLE 21

Eighteen grams of Toximal TA-15 surfactant were dissolved in water over a period of 1 hour. 2.8 grams of HYPOL® PreMA® G-50 hydrophilic prepolymer were added to the solution and allowed to mix for 180 minutes. 20 grams of glyphosate acid were added and the solution was neutralized with isopropylamine from a pH of 1.96 to 4.21. A stable, clear solution with a brownnish color (imparted by the surfactant) was obtained.

EXAMPLE 22

Thirty-six grams of glyphosate acid were added to 69 grams of water. 3.3 grams of HYPOL® PreMA® G-50 hydrophilic prepolymer were then added and the solution was allowed to stir for 20 minutes. The solution was neutralized to a pH of 5.00 with isopropylamine. The solution appeared very slightly cloudy but did not separate, indicating all components at this concentration to be compatible.

EXAMPLE 23

125 grams of 50% tallow ethoxylated amine (15 ethoxy equivalent), 20% polyethylene glycol 600, and 30% diethylene glycol/ethylene glycol was added to 1814.0 grams of water. 120 grams of HYPOL® PreMA® G-50 hydrophilic prepolymer were added and the solution was allowed to stir for 58 minutes. 219.2 grams of glyphosate acid were then added and the pH neutralized to 4.79 with isopropylamine. The temperature was recorded at 34° C. at this point. A clear stable solution was obtained.

EXAMPLE 24

At room temperature, 3 grams of HYPOL® PreMA® G-50 hydrophilic prepolymer was dissolved in 100 grams of water. One gram of this solution was then mixed with 100 grams of water, and 0.89 grams of "Home Orchard Spray", a commercially available fungicide/insecticide comprised of 14.% Captain, 7.5% Malathion and 15% Methoxychlor, was added to this mixture. Mixing was continued until all of the solid had been dissolved or dispersed. The resulting concentration is equivalent to the recommended concentration for the commercial use of this product.

The solution showed no signs of settling after mixing until after 24 hours. This is consistent with a control solution made using just the "Home Orchard Spray" and water at the recommended concentration.

EXAMPLE 25

At room temperature, 3 grams of HYPOL® PreMA® G-50 hydrophilic prepolymer was dissolved in 100 grams of water. 3.55 grams of this solution was then mixed with 100 grams of water, and 3.5 grams of "Funginex", a commercially available fungicide containing 6.5% Triforine was added to the solution. The solution was mixed until all of the fungicide was dissolved. The resulting concentration is equivalent to the recommended concentration for the commercial use of this product.

The solution showed no signs of settling after mixing until after 24 hours. This is consistent with a control solution made using just the fungicide and water at the recommended concentration.

EXAMPLE 26

At room temperature, 3 grams of HYPOL® PreMA® G-50 hydrophilic prepolymer was dissolved in 100 grams of water. 3.55 grams of this solution was then mixed with 100 grams of water, and 0.5 grams of "Sevin", a commercially available insecticide containing 21.3% Carbaryl was added to this mixture. The solution was mixed until all of the insecticide was dissolved. The resulting concentration is equivalent to the recommended concentration for the commercial use of this product.

The solution showed no signs of settling after mixing until after 24 hours. This is consistent with a control solution made using just the insecticide and water at the recommended concentration.

EXAMPLE 27

At room temperature, 3 grams of HYPOL® PreMA® G-50 hydrophilic prepolymer was dissolved in 100 grams of water. 3.55 grams of this solution was then mixed with 100 grams of water, and 0.5 grams of "Daconil", a commercially available fungicide containing 29.6% Chlorothalonil was added to this mixture. The solution was mixed until all of the fungicide was dissolved. The resulting concentration is equivalent to the recommended concentration for the commercial use of this product.

The solution showed no signs of settling after mixing until after 24 hours. This is consistent with a control solution made using just the fungicide and water at the recommended concentration.

EXAMPLE 28

At room temperature, 3 grams of HYPOL® PreMA® G-50 hydrophilic prepolymer was dissolved in 100 grams of water. 3.55 grams of this solution was then mixed with 100 grams of water, and 1.18 grams of "Bonidel", a commercially available insecticide containing 12.6% Chlorpyrifos was added to this mixture. The solution was mixed until all of the insecticide was dissolved. The resulting concentration is equivalent to the recommended concentration for the commercial use of this product.

The solution showed no signs of settling after mixing until after 24 hours. This is consistent with a control solution made using just the insecticide and water at the recommended concentration.

EXAMPLE 29

At room temperature, 4 grams of HYPOL® PreMA® G-50 hydrophilic prepolymer was dissolved in 50 grams of Option II, a liquid herbicide. This solution showed no signs of settling or gelling due to the presence of the prepolymer in the solution. Five grams of this mixture was then added to 195 grams of water, a milky solution resulted.

Neither solution showed signs of settling after mixing. The properties of the dilute solution were consistent with a control solution prepared using just Option II and water.

EXAMPLE 30

At room temperature, 0.3 grams of HYPOL® PreMA® G-50 hydrophilic prepolymer was dissolved in 100 grams of water. Four grams of Nicosulfuron, an insecticide, were added to the prepolymer and water solution and was mixed until the insecticide dissolved. The properties of this solution were consistent with a control solution prepared using just the insecticide and water, indicating compatibility with the prepolymer.

EXAMPLE 31

At room temperature, 0.9 grams of HYPOL® PreMA® G-50 hydrophilic prepolymer was dissolved in 300 grams of water. One gram of Propargite, an acaricide, was added to the prepolymer and water solution and was mixed until the acaricide dissolved. The properties of this solution were consistent with a control solution prepared using just the acaricide and water, indicating compatibility with the prepolymer.

EXAMPLE 32

At room temperature, 0.6 grams of HYPOL® PreMA® G-50 hydrophilic prepolymer was dissolved in 200 grams of water. 0.5 grams of Primisulfuron, a herbicide, was mixed with the 200 grams of the prepolymer and water solution. The solution was mixed and then 1 ml of Toximal TA-15 was added and the solution was mixed for an additional 30 minutes. A homogeneous mixture was never truly achieved. However, when a control solution was prepared using just the herbicide, water and Toximal TA-15 in the same sample ratios, a comparable non-homogeneous solution resulted.

EXAMPLE 33

At room temperature, 0.6 grams of HYPOL® PreMA® G-50 hydrophilic prepolymer was dissolved in 200 grams of water. 0.5 grams of Chloroimuron Ethyl, a herbicide, was mixed with the 200 grams of the prepolymer and water solution. The solution was mixed until it appeared that all of the herbicide had been dissolved. The properties of the solution were consistent with a control solution made using just the herbicide and water.

EXAMPLE 34

At room temperature, 0.6 grams of HYPOL® PreMA® G-50 hydrophilic prepolymer was dissolved in 200 grams of water. 0.5 grams of Thifensulfuron Methyl, a herbicide, was mixed with the 200 grams of the prepolymer and water solution. The solution was mixed until it appeared that all of the herbicide had been dissolved. The properties of the solution were consistent with a control solution made using just the herbicide and water.

EXAMPLE 35

At room temperature, 0.6 grams of HYPOL® PreMA® G-50 hydrophilic prepolymer was dissolved in 200 grams of water. 16 grams of Dicamba, a herbicide, was mixed with the 150 grams of the prepolymer and water solution. The solution was mixed until it appeared that all of the herbicide had been dissolved or dispersed. The solution showed quick settling of some undissolved solids and maintained a milky appearance. However, the solids stayed in solution longer than a control of just the herbicide and water.

EXAMPLE 36

At room temperature, 0.5 grams of HYPOL® PreMA® G-50 hydrophilic prepolymer was dissolved in 25 grams of Kelthane, a liquid Acaricide. This solution showed no signs of settling or gelling due to the presence of the prepolymer in the mixture. 10 grams of this mixture were added to 190 grams of water. No problems with mixing were seen. Neither solution showed signs of settling after mixing. The properties of the dilute solution were consistent with a control solution made using just the acaricide and water.

EXAMPLE 37

At room temperature, 0.3 grams of HYPOL® PreMA® G-50 hydrophilic prepolymer was dissolved in 100 grams of water. 15 grams of Acephate, an insecticide, were mixed with 85 grams of the prepolymer/water solution until it had appeared that all of the insecticide has been dissolved or dispersed. The solution was clear and showed no signs of settling with time. The properties of the solution were consistent with a control solution made using just the insecticide and water.

EXAMPLE 38

At room temperature, 6 grams of HYPOL® PreMA® G-50 hydrophilic prepolymer were dissolved in 94 grams of water. The solution was mixed for 15 minutes. 45 grams of Chloromequat, a plant growth regulator, were added to the mixture and mixed for an additional 15 minutes. There were no signs of settling or gelling of the mixture after mixing or with time indicating the compatibility of the components.

EXAMPLE 39

Sixty grams of HYPOL® PreMA® G-50 hydrophilic prepolymer were weighed into a container and dissolved in 240 grams of de-ionized water. The solution was then placed in a jacketed beaker whose temperature was kept at a constant 25° C. A magnetic stirrer was used to mix the solution in the temperature-controlled environment. At regular intervals, small aliquots (1 ml) of the solution were collected. These aliquots were immediately mixed with 5 ml of a 0.01N solution of Di-n-butylamine. The samples were mixed for at least 30 minutes using a magnetic stirrer. These samples were then placed in a 55° C. oven overnight until all the liquid in the sample had evaporated. Next, the samples were weighed and the weights recorded. A clear to white residue was visible on the bottom of all the sample vials. Next, 10 ml of water were added to each vial and allowed to sit for at least one hour. The liquid portion of the sample was then removed from the vial and placed into a pre-weighed aluminum weighing dish. The weight dish and vial were then placed in the 55° C. oven and were kept in the oven overnight and the water was allowed to evaporate. Each sample was weighed again and the new weight recorded. Changes in the weight from the original values were then calculated. The data showed that the percentage of the original solution that was dried in the vial and dissolved in the 10 ml of water decreased as the reaction was allowed to progress. The samples collected at the end of the reaction formed clearly stable gels that were hydrophilic and only partially soluble in water.

EXAMPLE 40

Thirty grams of HYPOL® PreMA® G-50 hydrophilic prepolymer were weighed into a container and dissolved in 270 grams of deionized water. The solution was then placed in a jacketed beaker whose temperature was kept at a constant 25° C. A magnetic stirrer was used to mix the solution in the temperature-controlled environment. At regular intervals, small aliquots (1 ml) of the solution were collected. These aliquots were immediately mixed with 5 ml of a 0.01N solution of Di-n-butylamine. The samples were mixed for at least 30 minutes using a magnetic stirrer. These samples were then placed in a 55° C. oven overnight until all the liquid in the sample had evaporated. Next, the samples were weighed and the weights recorded. A clear to white residue was visible on the bottom of all the sample vials. Next, 10 ml of water were added to each vial and allowed to sit for at least one hour. The liquid portion of the sample was then removed from the vial and placed into a pre-weighed aluminum weighing dish. The weight dish and vial were then placed in the 55° C. oven and were kept in the oven overnight and the water was allowed to evaporate. Each sample was weighed again and the new weight recorded. Changes in the weight from the original values were then calculated. The data showed that the percentage of the original solution that was dried in the vial and dissolved in the 10 ml of water decreased as the reaction was allowed to progress. The samples collected at the end of the reaction formed clearly stable gels that were hydrophilic and only partially soluble in water.

EXAMPLE 41

Twenty-seven grams of HYPOL® PreMA® G-50 hydrophilic prepolymer were weighed into a container and dissolved in 273 grams of de-ionized water. The solution was then placed in a jacketed beaker whose temperature was kept at a constant 25° C. A magnetic stirrer was used to mix the solution in the temperature-controlled environment. At regular intervals, small aliquots (1 ml) of the solution were collected. These aliquots were immediately mixed with 5 ml of a 0.01N solution of Di-n-butylamine. The samples were mixed for at least 30 minutes using a magnetic stirrer. These samples were then placed in a 55° C. oven overnight until all the liquid in the sample had evaporated. Next, the samples were weighed and the weights recorded. A clear to white residue was visible on the bottom of all the sample vials. Next, 10 ml of water were added to each vial and allowed to sit for at least one hour. The liquid portion of the sample was then removed from the vial and placed into a pre-weighed aluminum weighing dish. The weight dish and vial were then placed in the 55° C. oven and were kept in the oven overnight and the water was allowed to evaporate. Each sample was weighed again and the new weight recorded. Changes in the weight from the original values were then calculated. The data showed that the percentage of the original solution that was dried in the vial and dissolved in the 10 ml of water decreased as the reaction was allowed to progress. The samples collected at the end of the reaction formed clearly stable gels that were hydrophilic and only partially soluble in water.

EXAMPLE 42

Twenty-four grams of HYPOL® PreMA® G-50 hydrophilic prepolymer were weighed into a container and dissolved in 276 grams of de-ionized water. The solution was then placed in a jacketed beaker whose temperature was kept at a constant 25° C. A magnetic stirrer was used to mix the solution in the temperature-controlled environment. At regular intervals, small aliquots (1 ml) of the solution were collected. These aliquots were immediately mixed with 5 ml of a 0.01N solution of Di-n-butylamine. The samples were mixed for at least 30 minutes using a magnetic stirrer. These samples were then placed in a 55° C. oven overnight until all the liquid in the sample had evaporated. Next, the samples were weighed and the weights recorded. A clear to white residue was visible on the bottom of all the sample vials. Next, 10 ml of water were added to each vial and allowed to sit for at least one hour. The liquid portion of the sample was then removed from the vial and placed into a pre-weighed aluminum weighing dish. The weight dish and vial were then placed in the 55° C. oven and were kept in the oven overnight and the water was allowed to evaporate. Each sample was weighed again and the new weight recorded. Changes in the weight from the original values were then calculated. The data showed that the percentage of the original solution that was dried in the vial and dissolved in the 10 ml of water decreased as the reaction was allowed to progress. The samples collected at the end of the reaction formed clearly stable gels that were hydrophilic and only partially soluble in water.

EXAMPLE 43

Twenty-four grams of HYPOL® PreMA® G-50 hydrophilic prepolymer were weighed into a container and dissolved in 276 grams of de-ionized water. The solution was then placed in a jacketed beaker whose temperature was kept at a constant 25° C. A magnetic stirrer was used to mix the solution in the temperature-controlled environment. At regular intervals, small aliquots (1 ml) of the solution were collected. These aliquots were immediately mixed with 5 ml of a 0.01N solution of Di-n-butylamine. The samples were mixed for at least 30 minutes using a magnetic stirrer. These samples were then placed in a 55° C. oven overnight until all the liquid in the sample had evaporated. Next, the samples were weighed and the weights recorded. A clear to white residue was visible on the bottom of all the sample vials. Next, 10 ml of water were added to each vial and allowed to sit for at least one hour. The liquid portion of the sample was then removed from the vial and placed into a pre-weighed aluminum weighing dish. The weight dish and vial were then placed in the 55° C. oven and were kept in the oven overnight and the water was allowed to evaporate. Each sample was weighed again and the new weight recorded. Changes in the weight from the original values were then calculated. The data showed that the percentage of the original solution that was dried in the vial and dissolved in the 10 ml of water decreased as the reaction was allowed to progress. The samples collected at the end of the reaction formed clearly stable gels that were hydrophilic and only partially soluble in water.

EXAMPLE 44

Eight grams of HYPOL® PreMA® G-50 hydrophilic prepolymer were dissolved in 92 grams of water at 100° C., and the solution was mixed for seven hours. Next, 14.19 grams of FUNGINEX, a fungicide containing 6.5% Triforine, was added to 50 grams of the prepolymer/water solution. The solution was mixed and appeared homogeneous and continued to be so even after twenty-four hours. An aliquot of this solution was placed into an aluminum weighing dish and allowed to dry in a 60° C. oven overnight. A strong elastic film was obtained.

3.2 grams of the water/Triforine solution was diluted into two hundred grams of water. The resulting concentration of Triforine is equivalent to the recommended concentration for the commercial use of the product. A stable solution was obtained and an aliquot placed into an aluminum weighing dish and allowed to dry in a 60° C. oven overnight. An elastic film was obtained.

EXAMPLE 45

Eight grams of HYPOL® PreMA® G-50 hydrophilic prepolymer were dissolved in 92 grams of water at 25° C., and the solution was mixed for seven hours. Next, 56.76 grams of SEVIN, an insecticide containing 21.3% Carbaryl, was added to 150 grams of the prepolymer/water solution. The solution was mixed and appeared homogeneous and continued to be so even after twenty-four hours. An aliquot of this solution was placed into an aluminum weighing dish and allowed to dry in a 60° C. oven overnight. A strong elastic film was obtained.

2.06 grams of the water/Carbaryl solution was diluted into 120 grams of water. The resulting concentration of Carbaryl is equivalent to the recommended concentration for the commercial use of the product. A stable solution was obtained and an aliquot placed into an aluminum weighing dish and allowed to dry in a 60° C. oven overnight. An elastic film was obtained.

EXAMPLE 46

Eight grams of HYPOL® PreMA® G-50 hydrophilic prepolymer were dissolved in 92 grams of water at 25° C., and the solution was mixed for seven hours. Next, 28.38 grams of DACONIL, a fungicide containing 29.6% Chlorothalonil, was added to 75 grams of the prepolymer/water solution. The solution was mixed and appeared homogeneous and continued to be so even after twenty-four hours. An aliquot of this solution was placed into an aluminum weighing dish and allowed to dry in a 60° C. oven overnight. A strong elastic film was obtained.

2.06 grams of the water/Chlorothalonil solution was diluted into 120 grams of water. The resulting concentration of Chlorothalonil is equivalent to the recommended concentration for the commercial use of the product. A stable solution was obtained and an aliquot placed into an aluminum weighing dish and allowed to dry in a 60° C. oven overnight. An elastic film was obtained.

What is claimed is:

1. A pesticidal composition, comprising an aqueous solution of a pesticidally effective amount of a pesticide; and a subgelation amount of a hydratable gel-forming hydrophilic polyurethane or polyurea-urethane polymer.

2. The pesticidal composition of claim 1, wherein said hydrophilic polymer is formed from a prepolymer selected from the group consisting of toluene diisocyanate-polyethylene glycol-timethylolpropane, methylene diisocyanate-methylene diisocyanate homopolymer-polymeric methylene diisocyanate-polyethylene glycol, toluene diisocyanate and polymer of ethylene oxide and propylene oxide with trimethylolpropane, isophorone diisocyanate and polymer of ethylene oxide-propylene oxide-trimethylolpropane, toluene diisocyanate polyethylene glycol trilactate, and polyethylene glycol end capped with toluene diisocyanate.

3. The pesticidal composition of claim 1, further comprising an additive selected from the group consisting of polyethylene glycol, diethylene glycol, ethylene glycol, methanol, ethanol, 2-propanol, n-propanol, butanol, hexanol and heptanol.

4. The pesticidal composition of claim 1, further comprising an effective amount of an activating surfactant.

5. The pesticidal composition of claim 4, wherein said surfactant is selected from the group consisting of alkyl benzene and alkyl naphthalene sulfonates, alkyl phenol polyoxyethylene, sulfated fatty alcohols, amines, acid amides, long chain acid esters of sodium isethionate, esters of sodium sulfosuccinate, sulfated or sulfonated fatty acid esters petroleum sulfonates, N-acyl amino acids, alkyl polyglycosides, alkyl ethoxylated amines, alkylethoxylated alcohols, and mixtures of alkyl or alkylaryl quaternary amines.

6. A delivery system for delivering a pesticidal composition to a substrate, said delivery system comprising an aqueous solution of a subgelation amount of a hydratable gel-forming hydrophilic polymer selected from the group consisting of polyurea-urethane, and polyurethane, and a pesticidally effective amount of a pesticide; and means for delivering said solution to said substrate.

7. The delivery system of claim 6, wherein said pesticide is a member selected from the group consisting of an insecticide, a herbicide, a nematocide, a fungicide, a plant regulator, a defoliant, and a desiccant.

8. The delivery system of claim 6, further comprising an effective amount of an activiating surfactant.

9. The delivery system of claim 8, wherein said surfactant is selected from the group consisting of alkyl benzene and alkyl naphthalene sulfonates, alkyl phenol polyoxyethylene, sulfated fatty alcohols, amines, acid amides, long chain acid esters of sodium isethionate, esters of sodium sulfosuccinate, sulfated or sulfonated fatty acid esters petroleum sulfonates, N-acyl amino acids, alkyl polyglycosides, alkyl ethoxylated amines, alkylethoxylated alcohols, and mixed alkyl or alkylarylquaternary amines.

10. A method of formulating a pesticidal composition, comprising forming a reaction product of a hydrophilic polymer formed from a prepolymer selected from the group consisting of polyurea-urethane, polyurea and polyurethane and an activating surfactant; and adding to said reaction product a pesticidally effective amount of a pesticide.

11. A method of controlling pests, comprising administering to said pests or the locus thereof an effective amount of a composition comprising an aqueous solution of a pesticidally effective amount of a pesticide and a subgelation amount of a hydratable gel-forming hydrophilic polyurethane or polyurea-urethane polymer.

12. The method of claim 11, wherein said composition further comprises an effective amount of an activating surfactant.

13. The method of claim 12, wherein said surfactant selected from the group consisting of alkyl benzene and alkyl naphthalene sulfonates, alkyl phenol polyoxyethylene, sulfated fatty alcohols, amines, acid amides, long chain acid esters of sodium isethionate, esters of sodium sulfosuccinate, sulfated or sulfonated fatty acid esters petroleum sulfonates, N-acyl amino acids, alkyl polyglycosides, alkyl ethoxylated amines, alkylethoxylated alcohols, and mixed alkyl or alkylarylquaternary amines.

14. A pesticidal composition comprising an elastic film formed upon the evaporation of water from an aqueous solution of a pesticidally effective amount of a pesticide and a subgelation amount of a hydratable gel-forming hydrophilic polyurethane or polyurea-urethane polymer.

15. The pesticidal composition of claim 14, wherein said aqueous solution further comprises an activating surfactant.

16. The pesticidal composition of claim 14, wherein said hydrophilic polymer is formed from a prepolymer selected from the group consisting of toluene diisocyanate-polyethylene glycol-trimethylolpropane, methylene diisocyanate-methylene diisocyanate homopolymer-polymeric methylene diisocyanate-polyethylene glycol, toluene diisocyanate and polymer of ethylene oxide and propylene oxide with trimethylolpropane, isophorone diisocyanate and polymer of ethylene oxide-propylene oxide-trimethylolpropane, toluene diisocyanate polyethylene glycol trilactate, and polyethylene glycol end capped with toluene diisocyanate.

17. The pesticidal composition of claim 15, wherein said surfactant is selected from the group consisting of alkyl benzene and alkyl naphthalene sulfonates, alkyl phenol polyoxyethylene, sulfated fatty alcohols, amines, acid amides, long chain acid esters of sodium isethionate, esters of sodium sulfosuccinate, sulfated or sulfonated fatty acid esters petroleum sulfonates, N-acyl amino acids, alkyl polyglycosides, alkyl ethoxylated amines, alkylethoxylated alcohols, and mixtures of alkyl or alkylaryl quaternary amines.

* * * * *